United States Patent
Liao et al.

(10) Patent No.: US 9,456,259 B1
(45) Date of Patent: Sep. 27, 2016

(54) PHYSIOLOGICAL MONITORING SYSTEM USING BLUETOOTH LOW ENERGY MESH NETWORK

(71) Applicant: FLYTECH TECHNOLOGY CO., LTD, Taipei (TW)

(72) Inventors: Jui-Tsung Liao, Taipei (TW); Kun-Hsiung Wu, Taipei (TW)

(73) Assignee: FLYTECH TECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 14/962,352

(22) Filed: Dec. 8, 2015

(30) Foreign Application Priority Data

Nov. 6, 2015  (TW) .............................. 104136707 A

(51) Int. Cl.
| | |
|---|---|
| G08C 19/22 | (2006.01) |
| H04Q 9/00 | (2006.01) |
| H04W 4/00 | (2009.01) |
| H04W 84/18 | (2009.01) |

(52) U.S. Cl.
CPC .............. *H04Q 9/00* (2013.01); *H04W 4/008* (2013.01); *H04Q 2209/43* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 2008/0214903 A1* | 9/2008 | Orbach | G06Q 50/22 600/301 |
| 2013/0317753 A1* | 11/2013 | Kamen | G06F 19/3412 702/19 |
| 2015/0363563 A1* | 12/2015 | Hallwachs | G06F 19/3406 705/3 |
| 2016/0029890 A1* | 2/2016 | Stump | A61B 5/0022 600/301 |

* cited by examiner

*Primary Examiner* — Adolf Dsouza
(74) *Attorney, Agent, or Firm* — WPAT, PC; Justin King

(57) ABSTRACT

A physiological monitoring system using a Bluetooth low energy mesh network is provided. The physiological monitoring system includes a main control device and plural physiological detection devices. The main control device broadcasts a measurement command signal through the Bluetooth low energy mesh network. After the measurement command signal is received by the plural physiological detection devices, physiological data signals of corresponding subjects are generated and externally broadcasted through the Bluetooth low energy mesh network. After the physiological data signals are received by the main control device, medical record tables corresponding to the subject are generated.

13 Claims, 3 Drawing Sheets

PHYSIOLOGICAL MONITORING SYSTEM USING BLUETOOTH LOW ENERGY MESH NETWORK

FIELD OF THE INVENTION

The present invention relates to a physiological monitoring system, and more particularly to a physiological monitoring system using a Bluetooth low energy mesh network.

BACKGROUND OF THE INVENTION

With increasing development of modern medical science and technology, aging population and declining fertility rate, modern societies gradually become aged societies and thus the improvement of health care demands is needed. That is, the health care needs for the elderly population gradually increase. In addition, the health care needs for the patients due to illness and for the physically disabled persons due to accident also gradually increase.

Nowadays, the number of medical personnel cannot comply with the increasing needs for medical care. Even if the medical personnel work overtime, the immediate measures to provide medical care cannot be taken and thus the medical quality is impaired. For example, the process of measuring the patients' physiological values such as the blood pressure values is an indispensable process during the medical care period. For example, health care workers have to go to the wards to periodically and successively measure the physiological values and record the physiological values on papers, and then go back to the nursing station to input the physiological values to a computer for filing. Because of the routine manual measurement tasks, a large number of health care workers cannot provide health care services more actively.

Therefore, there is a need of providing a novel physiological monitoring system in order to overcome the above drawbacks.

SUMMARY OF THE INVENTION

An object of the present invention provides a physiological monitoring system using a Bluetooth low energy mesh network in order to overcome the drawbacks of the conventional technology.

In accordance with an aspect of the present invention, there is provided a physiological monitoring system using a Bluetooth low energy mesh network. The physiological monitoring system includes a main control device and plural physiological detection devices. The main control device includes a data processor and a main control terminal Bluetooth low energy transmission module. The data processor generates a measurement command signal. The measurement command signal contains an identification code of the main control device. After the measurement command signal is received by the main control terminal Bluetooth low energy transmission module, the measurement command signal is externally broadcasted. Each physiological detection device includes a peripheral terminal Bluetooth low energy transmission module receiving the measurement command signal, a detection processor and a physiological sensor. After the measurement command signal is received by the detection processor through the Bluetooth low energy mesh network, the measurement command signal is transmitted to the physiological sensor. A physiological value of a subject is detected by the physiological sensor according to the measurement command signal, and then the physiological value is transmitted to the detection processor. A physiological data signal is generated by the detection processor according to the physiological value and an identification code of the physiological detection device, and the physiological data signal is externally broadcasted through the peripheral terminal Bluetooth low energy transmission module. After the physiological data signal is received by the main control terminal Bluetooth low energy transmission module of the main control device through the Bluetooth low energy mesh network, the data processor generates a medical record table corresponding to the subject according to the physiological data signal.

In an embodiment, the main control device further includes a warning device, and the data processor determines whether a warning drive signal is generated according to the medical record table. The warning device is driven to issue a warning notification signal in response to the warning drive signal.

In an embodiment, the warning device is light alarm or a buzzer.

In an embodiment, the measurement command signal from the main control device further contains a speech driving signal, and each physiological detection device further includes a speech input/output device. After the speech driving signal is decoded by the detection processor, a corresponding speed information is broadcasted by the speech input/output device.

In an embodiment, the physiological detection device further includes an input device. When the detection processor receives a responding command through the input device, the detection processor enables the physiological sensor to detect the physiological value of the subject.

In an embodiment, the medical record table contains a device address field and a physiological value field. According to the received physiological data signal, the data processor records the identification code of the physiological detection device into the device address field and records the physiological value into the physiological value field corresponding to the identification code of the physiological detection device.

In an embodiment, the main control device further includes a physiological data evaluation unit and a warning device. The physiological data evaluation unit judges whether the physiological value lies in a reference value range, thereby determining whether the data processor issues a warning drive signal to drive the warning device.

In an embodiment, the physiological value includes a heart rate, a blood pressure value or a body temperature.

In an embodiment, the physiological monitoring system further includes at least one fixed terminal Bluetooth low energy transmission device. The at least one fixed terminal Bluetooth low energy transmission device is arranged between the main control device and the plural physiological detection devices, so that a transmission path of externally broadcasting the measurement command signal and the physiological data signal is expanded.

In an embodiment, the physiological monitoring system further includes a cloud database. The medical record table is stored in the cloud database.

In an embodiment, the physiological detection device is a wearable device.

In an embodiment, the wearable device further includes a detector, and the detector is electrically connected with the detection processor. When the wearable device is detached from the subject, the detection processor notifies the main control device.

In an embodiment, the physiological detection device further includes at least one quick response code or a near field communication tag that provides an information of the subject of the physiological detection device.

From the above descriptions, the physiological monitoring system of the present invention uses a Bluetooth low energy mesh network to transmit signal in a broadcasting manner. The low energy Bluetooth has many benefits such as low power consumption, low cost and high operation speed. Moreover, all devices in the mesh network can transmit and receive signals between each other through the serial connection between the devices or intermediate nodes (e.g., the fixed terminal Bluetooth low energy transmission devices). Consequently, the signal transmission is not restricted to specified distance and range while meeting the low energy requirements of the medical facilities. Moreover, the physiological monitoring system of the present invention further provides the mechanism of transmitting the speed information and the mechanism of allowing the subject to input the responding command. Consequently, the subject can realize that a detecting process will be performed on the subject and determine whether the detecting process is accepted or not. In other words, the detecting safety in the automatic measurement process is enhanced.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments and accompanying drawings.

Figure 1A:
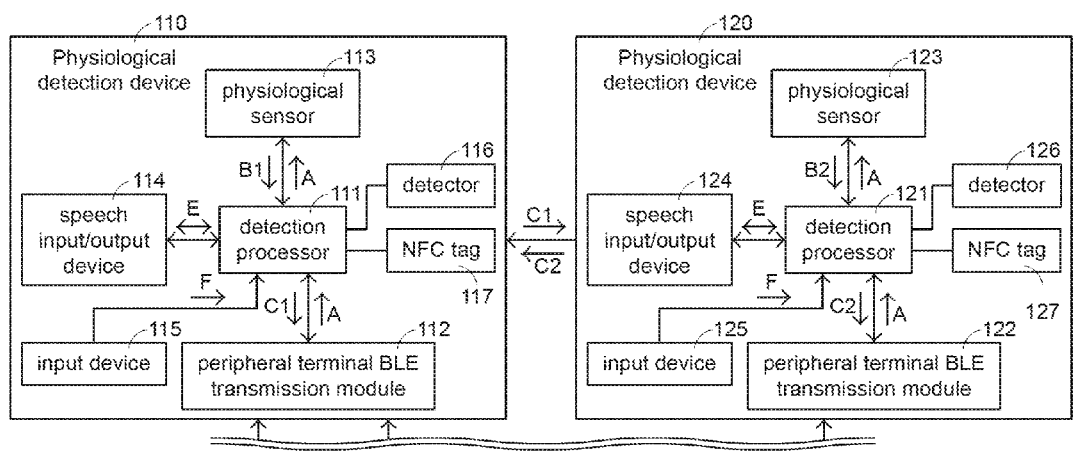
FIGS. 1A & 1B are schematic functional block diagram illustrating a physiological monitoring system using a Bluetooth low energy mesh network according to an embodiment of the present invention.
Figure 1B:
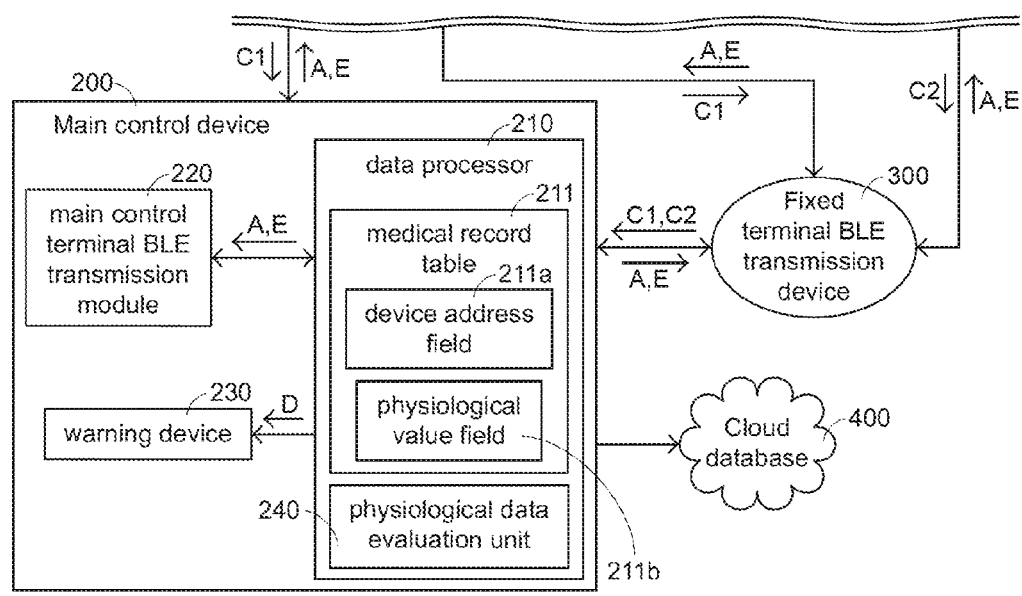

FIGS. 1A & 1B are schematic functional block diagram illustrating a physiological monitoring system using a Bluetooth low energy mesh network according to an embodiment of the present invention. In this context, the term "Bluetooth low energy mesh network" is abbreviated to a "BLE mesh network".

As shown in FIGS. 1A & 1B, the physiological monitoring system using the BLE mesh network comprises a main control device 200, plural physiological detection devices 110, 120, a fixed terminal Bluetooth low energy transmission device 300 and a cloud database 400. The main control device 200 comprises a main control terminal Bluetooth low energy transmission module 220, a data processor 210, a warning device 230 and a physiological data evaluation unit 240, which are electrically connected with each other. The physiological detection device 110 comprises a peripheral terminal Bluetooth low energy transmission module 112, a detection processor 111, a physiological sensor 113, a speech input/output device 114 and an input device 115, which are electrically connected with each other. The physiological detection device 120 comprises a peripheral terminal Bluetooth low energy transmission module 122, a detection processor 121, a physiological sensor 123, a speech input/output device 124 and an input device 125, which are electrically connected with each other.

Hereinafter, the basic operations of the physiological monitoring system will be illustrated with reference to FIGS. 1A & 1B. For example, the physiological monitoring system of the present invention can be applied to a health care center. As mentioned above, the health care workers have to go to the wards to measure the patients' physiological values in person according to the conventional technology. In contrast, the health care worker can use the physiological monitoring system of the present invention to measure the patients' physiological values without the need of going to the wards in person. For measuring the patients' physiological values, the health care worker may firstly operate the main control device 200 in a nursing station (e.g., a computer in the nursing station) to issue a measurement command signal A. For example, the measurement command signal A is a program code containing an identification code of the main control device. According to the identification code of the main control device, the physiological detection devices can recognize that the measurement command signal A is issued from the main control device. In particular, the measurement command signal A is generated by the data processor 210, and then externally broadcasted by the main control terminal Bluetooth low energy transmission module 220. The broadcasted measurement command signal A can be received by the physiological detection devices 110 and 120 through the fixed terminal Bluetooth low energy transmission device 300, or the broadcasted measurement command signal A can be directly received by the physiological detection devices 110 and 120. Each physiological detection device is correlated with a corresponding subject (or a patient). In accordance with the present invention, the wireless medical network for the health care center has to comply with the requirement of low energy and low radio frequency interference. Consequently, the physiological monitoring system of the present invention uses the BLE mesh network to transmit signals between the main control device and the physiological detection device. In addition, if the main control device is far from the physiological detection device, the physiological monitoring system is further equipped with the fixed terminal Bluetooth low energy transmission device 300 to expand the signal transmission range and the signal transmission stability.

In an embodiment, the measurement command signal A contains a speech driving signal E, and the physiological detection device 110 contains default speed information. After the speech driving signal E is received by the physiological detection device 110, the speech driving signal E is transmitted to the detection processor 111. In response to the speech driving signal E of the measurement command signal A, the detection processor 111 drives the speech input/output device 114 (e.g., a speaker) to broadcast the default speed information. For example, the content of the default speed information includes an inquiry from the health care worker to inquire the subject whether a blood pressure measuring operation is done. After the subject hears the content of the default speed information, the subject may input a responding command F into the physiological detection device 110 through the input device 115 (e.g., a touch screen). Then, the responding command F is transmitted to the detection processor 111. According to the responding command F, the detection processor 111 determines whether the measurement command signal A is transmitted to the physiological sensor 113. If the responding command F indicates the message "No" or no responding command F is generated, the detection processor 111 does not transmit the measurement command signal A to the physiological sensor 113. Whereas, if the responding command F indicates the message "Yes", the detection processor 111 transmits the measurement command signal A to the physiological sensor 113. According to the measurement command signal A, a physiological value B1 of the subject is detected by the physiological sensor 113. The physiological value B1 is transmitted back to the detection processor 111. Then, a physiological data signal C1 is generated by the detection processor 111 according to the physiological value B1 and an identification code of the physiological detection device 110, and the physiological data signal C1 is externally broadcasted through the peripheral terminal Bluetooth low energy transmission module 112. Similarly, while the physiological detection device 111 performs the blood pressure measuring operation on another subject, a physiological value B2 of the subject and a physiological data signal C2 are acquired.

Due to the mechanism of transmitting the speed information and the mechanism of allowing the subject to input the responding command, the subject can realize that a detecting process will be performed on the subject and determine whether the detecting process is accepted or not. Consequently, the systematic safety of the physiological monitoring system is enhanced. For example, during the process of measuring the blood pressure, the gasbag wound around the arm or wrist of the subject is inflated. The inflated gasbag may oppress the blood vessel of the subject and discomfort the subject. If the subject judges that the current body condition is not feasible for the blood pressure measurement or the current scenario is not feasible for the blood pressure measurement, the subject can input the corresponding responding command to reject the blood pressure measurement. Consequently, the possibility of injuring the subject in the improper condition is minimized.

After the physiological data signals C1 and C2 are received by the main control device 200, the subsequent steps will be described. In particular, the physiological data signals C1 and C2 are received by the main control terminal Bluetooth low energy transmission module 220 of the main control device 200 and then transmitted to the data processor 210. According to the physiological data signals C1 and C2, the data processor 210 generates medical record tables 211 corresponding to the subjects. The medical record table 211 contains a device address field 211a and a physiological value field 211b. According to the received physiological data signals C1 and C2, the data processor 210 records the identification codes of the physiological detection devices 110 and 120 into the device address fields 211a, and records the physiological values B1 and B2 (e.g., blood pressure values, heart rates or body temperatures) into the physiological value fields 211b corresponding to the identification codes of the physiological detection devices 110 and 120. In particular, the device address fields 211a correspond to the subjects of the physiological detection devices 110 and 120. According to the identification codes of the physiological detection devices 110 and 120 in the device address fields 211a (e.g., the IP addresses of the physiological detection devices 110 and 120), the names of the subjects are realized and the medical record tables 211 corresponding to the subjects of the physiological detection devices 110 and 120 are generated. Afterwards, the medical record tables 211 can be stored into the cloud database 400.

From the above descriptions, the physiological monitoring system of the present invention uses the Bluetooth low energy mesh network to automatically search the physiological values of the subjects. Consequently, the measurement process is quickly performed, the medical record tables are automatically generated, the human resources of the health care workers is saved, the health care efficiency is enhanced, and the human error is reduced.

In this embodiment, the physiological detection device 110 further comprises a detector 116 and a near field communication (NFC) tag 117, and the physiological detection device 120 further comprises a detector 126 and a NFC tag 127. The detector 116 is electrically connected with the detection processor 111 for detecting whether the physiological detection device 110 is detached from the installation position. Similarly, the detector 126 is electrically connected with the detection processor 121 for detecting whether the physiological detection device 120 is detached from the installation position. For example, the physiological detection devices 110 and 120 are wearable devices that are worn on the wrists or arms of the subjects for detecting the physiological values of the subjects. If the physiological detection device 110 or 120 is detached from the subject, the detector 116 or 126 issues a notification signal to the main control device 200 through the detection processor 111 or 121. Consequently, the health care worker can go to the ward to realize the condition of the subject immediately. The NFC tag 117 is located at a side of the physiological detection device 11, and the NFC tag 127 is located at a side of the physiological detection device 12. Preferably but not exclusively, the NFC tags 117 and 127 are quick response codes. If the physiological detection device 110 or 120 is detached from the subject, the health care worker can inquire the NFC tag 117 or 127 about the subject corresponding to the physiological detection device 110 or 120. Consequently, while the physiological detection device 110 or 120 is worn on or installed on the subject, the possibility of erroneously detecting the physiological value will be minimized.

In this embodiment, the main control device 200 further comprises the warning device 230 and the physiological data evaluation unit 240. The physiological data evaluation unit 240 is used for judging whether the physiological values B1 and B2 (e.g., blood pressure values, heart rates or body temperatures) lie in a reference value range in order to determine whether the data processor 210 issues a warning drive signal D to drive the warning device 230. The reference value range is the human physiological range value in the normal condition. For example, the normal body temperature is in the range between 36 and 37.5 degrees Celsius, and the normal blood pressure is defined as a systolic pressure below 120 mmHg and a diastolic pressure below 80 mmHg. If the received physiological value is beyond the normal value range, the warning device 230 issues a warning notification signal to warn the health care workers to perform proper treatment. In other words, the physiological monitoring system of the present invention can facilitate warning and processing the health care immediately and increase the health care safety. In an embodiment, the warning device 230 is a light alarm, and the warning notification signal is the flash of red light. In another embodiment, the warning device 230 is a buzzer, and the warning notification signal is a sound.

Figure 2:
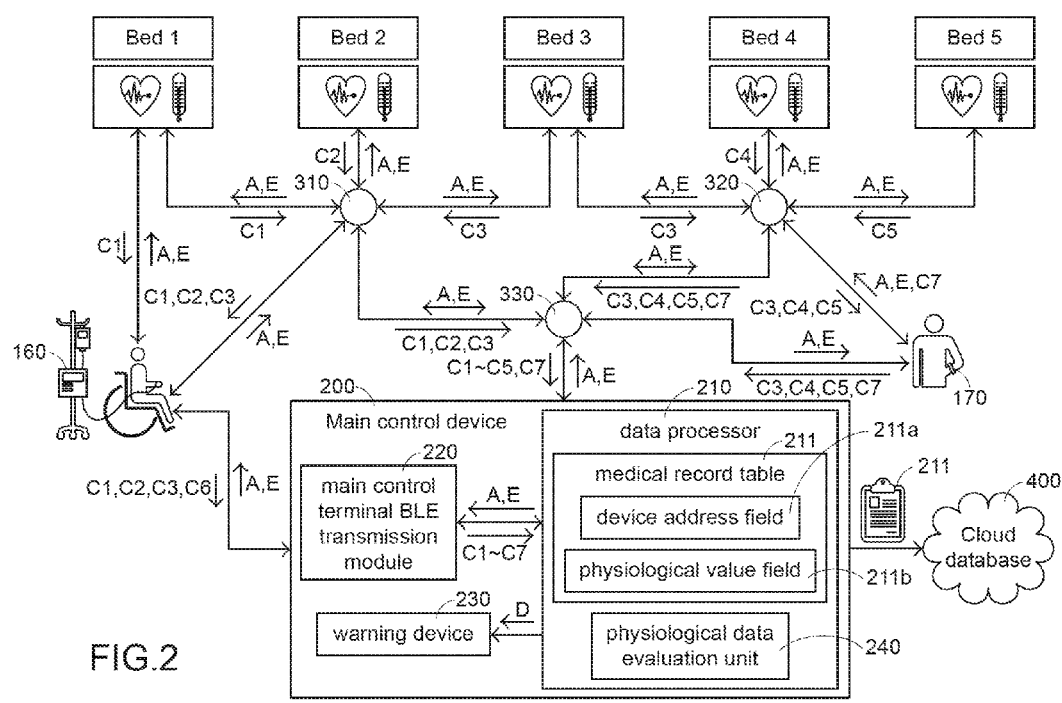
FIG. 2 schematically the architecture of the physiological monitoring system of FIGS. 1A & 1B applied to a health care center.

Hereinafter, the application of the physiological monitoring system to a health care center will be illustrated with reference to FIG. 2. FIG. 2 schematically the architecture of the physiological monitoring system of FIGS. 1A & 1B applied to a health care center. The paths of the measurement command signal A (i.e., from the main control device 200) and the physiological data signals C1~C7 (i.e., from the physiological detection devices 110~170) broadcasted through the BLE mesh network are also shown in FIG. 2. Consequently, the process of transferring the physiological data signals by the physiological monitoring system will be described in more details.

As shown in FIG. 2, the plural physiological detection devices 110~170 are installed in the health care center. In practice, these physiological detection devices are installed according to the usage conditions of the patients. In this embodiment, the physiological detection devices 110~150 are fixed on the hospital beds 1~5, the physiological detection device 160 is installed on a movable wheelchair, and the physiological detection device 170 is a wearable device worn on a patient. For complying with the specification of the network transmission energy in the health care center, the effective transmission distance of the BLE mesh network used in the physiological monitoring system of the present invention has limitations. Consequently, if the distance between the main control device and the physiological detection device is very long, the necessary broadcasting signal is possibly lost. For example, in case that the main control device is installed in the nursing station and the physiological detection devices installed on the hospital beds or worn on the patients are distributed in different floors, the broadcasting signals are possibly lost. For solving the above drawbacks, the physiological monitoring system of the present invention further comprises plural fixed terminal Bluetooth low energy transmission devices 310~330. The plural fixed terminal Bluetooth low energy transmission devices 310~330 are arranged between the main control device 320 and the plural physiological detection devices 110~170 in order to intermediately receive and transfer the broadcasting signals.

When the health care worker intends to measure of the physiological values of the patients, the health care worker may operate the main control device 200 in the nursing station to externally broadcast the measurement command signal A. The measurement command signal A is issued in a broadcasting manner. That is, the measurement command signal A is not exclusively transmitted to a specified object. Any physiological detection device and any fixed terminal Bluetooth low energy transmission device within the effective network transmission range can receive the measurement command signal A from the main control device 200. For example, as shown in FIG. 2, the physiological detection device 160 is within the effective network transmission range of the main control device 200. Consequently, the physiological detection device 160 can directly receive the measurement command signal A from the main control device 200. Moreover, since the fixed terminal Bluetooth low energy transmission device 330 is also within the effective network transmission range of the main control device 200, the fixed terminal Bluetooth low energy transmission device 330 can directly receive the measurement command signal A from the main control device 200 and externally broadcast the measurement command signal A. Moreover, the fixed terminal Bluetooth low energy transmission devices 310 and 320 and the physiological detection device 170 are within the effective network transmission range of the fixed terminal Bluetooth low energy transmission device 330. Consequently, the fixed terminal Bluetooth low energy transmission devices 310 and 320 and the physiological detection device 170 can receive the measurement command signal A from the fixed terminal Bluetooth low energy transmission device 330 and externally broadcast the measurement command signal A. Similarly, since the physiological detection devices 110 and 120 are within the effective network transmission range of the fixed terminal Bluetooth low energy transmission device 310, the physiological detection devices 110 and 120 can receive the measurement command signal A from the fixed terminal Bluetooth low energy transmission device 310. Similarly, since the physiological detection devices 130, 140 and 150 are within the effective network transmission range of the fixed terminal Bluetooth low energy transmission device 320, the physiological detection devices 130, 140 and 150 can receive the measurement command signal A from the fixed terminal Bluetooth low energy transmission device 320.

Similarly, the physiological data signals C1~C7 from the physiological detection devices 110~170 are externally broadcasted by the physiological detection devices 110~170. After these physiological data signals C1~C7 are received by the corresponding fixed terminal Bluetooth low energy transmission devices 310~330 within the effective network transmission ranges of the physiological detection devices 110~170, these physiological data signals C1~C7 are externally broadcasted to be received by the main control device 200.

From the above descriptions, the physiological monitoring system of the present invention uses a BLE mesh network to transmit signal in a broadcasting manner. The low energy Bluetooth has many benefits such as low power consumption, low cost and high operation speed. Moreover, all devices in the mesh network can transmit and receive signals between each other through the serial connection between the devices or intermediate nodes (e.g., the fixed terminal Bluetooth low energy transmission devices). Consequently, the signal transmission is not restricted to specified distance and range while meeting the low energy requirements of the medical facilities.

Moreover, the physiological monitoring system of the present invention further provides the mechanism of transmitting the speed information and the mechanism of allowing the subject to input the responding command. Consequently, the subject can realize that a detecting process will be performed on the subject and determine whether the detecting process is accepted or not. In other words, the detecting safety in the automatic measurement process is enhanced.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A physiological monitoring system using a Bluetooth low energy mesh network, the physiological monitoring system comprising:
   a main control device comprising a data processor and a main control terminal Bluetooth low energy transmission module, wherein the data processor generates a measurement command signal, and the measurement command signal contains an identification code of the main control device, wherein after the measurement command signal is received by the main control terminal Bluetooth low energy transmission module, the measurement command signal is externally broadcasted; and
   plural physiological detection devices, wherein each physiological detection device comprises a peripheral terminal Bluetooth low energy transmission module receiving the measurement command signal, a detection processor and a physiological sensor, wherein after the measurement command signal is received by the detection processor through the Bluetooth low energy mesh network, the measurement command signal is transmitted to the physiological sensor, wherein a physiological value of a subject is detected by the physiological sensor according to the measurement command signal, and then the physiological value is transmitted to the detection processor, wherein a physiological data signal is generated by the detection processor according to the physiological value and an identification code of the physiological detection device, and the physiological data signal is externally broadcasted through the peripheral terminal Bluetooth low energy transmission module, wherein after the physiological data signal is received by the main control terminal Bluetooth low energy transmission module of the main control device through the Bluetooth low energy mesh network, the data processor generates a medical record table corresponding to the subject according to the physiological data signal.

2. The physiological monitoring system according to claim 1, wherein the main control device further comprises a warning device, and the data processor determines whether a warning drive signal is generated according to the medical record table, wherein the warning device is driven to issue a warning notification signal in response to the warning drive signal.

3. The physiological monitoring system according to claim 2, wherein the warning device is light alarm or a buzzer.

4. The physiological monitoring system according to claim 1, wherein the measurement command signal from the main control device further contains a speech driving signal, and each physiological detection device further comprises a speech input/output device, wherein after the speech driving signal is decoded by the detection processor, a corresponding speed information is broadcasted by the speech input/output device.

5. The physiological monitoring system according to claim 1, wherein the physiological detection device further comprises an input device, wherein when the detection processor receives a responding command through the input device, the detection processor enables the physiological sensor to detect the physiological value of the subject.

6. The physiological monitoring system according to claim 1, wherein the medical record table contains a device address field and a physiological value field, wherein according to the received physiological data signal, the data processor records the identification code of the physiological detection device into the device address field and records the physiological value into the physiological value field corresponding to the identification code of the physiological detection device.

7. The physiological monitoring system according to claim 6, wherein the main control device further comprises a physiological data evaluation unit and a warning device, wherein the physiological data evaluation unit judges whether the physiological value lies in a reference value range, thereby determining whether the data processor issues a warning drive signal to drive the warning device.

8. The physiological monitoring system according to claim 1, wherein the physiological value includes a heart rate, a blood pressure value or a body temperature.

9. The physiological monitoring system according to claim 1, further comprising at least one fixed terminal Bluetooth low energy transmission device, wherein the at least one fixed terminal Bluetooth low energy transmission device is arranged between the main control device and the plural physiological detection devices, so that a transmission path of externally broadcasting the measurement command signal and the physiological data signal is expanded.

10. The physiological monitoring system according to claim 1, further comprising a cloud database, wherein the medical record table is stored in the cloud database.

11. The physiological monitoring system according to claim 1, wherein the physiological detection device is a wearable device.

12. The physiological monitoring system according to claim 11, wherein the wearable device further comprises a detector, and the detector is electrically connected with the detection processor, wherein when the wearable device is detached from the subject, the detection processor notifies the main control device.

13. The physiological monitoring system according to claim 1, wherein the physiological detection device further comprises at least one quick response code or a near field communication tag that provides an information of the subject of the physiological detection device.

* * * * *